United States Patent [19]

Twinn et al.

[11] Patent Number: 5,270,043
[45] Date of Patent: Dec. 14, 1993

[54] ARTHROPODICIDAL COMPOSITION COMPRISING THIODICARB AND A PHENYLPYRAZOLE

[75] Inventors: David C. Twinn; Timothy W. Green, both of Ongar, England

[73] Assignee: Rhone-Poulenc Agriculture Ltd., Ongar, United Kingdom

[21] Appl. No.: 631,948

[22] Filed: Dec. 21, 1990

[30] Foreign Application Priority Data

Dec. 22, 1989 [GB] United Kingdom ............... 8929101

[51] Int. Cl.$^5$ .................. A01N 25/00; A01N 43/56; A01N 47/12
[52] U.S. Cl. .................. 424/405; 514/403; 514/404; 514/406; 514/407; 514/508; 514/607
[58] Field of Search ............... 424/405; 514/403, 404, 514/607, 508, 406, 407

[56] References Cited

U.S. PATENT DOCUMENTS 4,260,775  4/1981  Plath et al. ............... 548/362
4,490,390 12/1984  Priester et al. ............ 514/508
4,614,533  9/1986  Schallner et al. .......... 71/92
4,771,066  9/1988  Gehring et al. ............ 514/404
4,772,310  9/1988  Stetler et al. ............. 71/92

FOREIGN PATENT DOCUMENTS 0008474  3/1980  European Pat. Off. .
0295117 12/1988  European Pat. Off. .
55-004352  1/1980  Japan .
55-009038  1/1980  Japan .

Primary Examiner—Thurman K. Page
Assistant Examiner—Robert H. Harrison
Attorney, Agent, or Firm—James G. Passé

[57] ABSTRACT

The invention provides arthropodicidal compositions comprising an arthropodicidally effective amount of (A) 5-amino-3-cyano-1-(2,6-dichloro-4-trifluoromethylphenyl)-4-trifluoromethylsulfinylpyrazole and (B) thiodicarb, and methods of controlling arthropod pests utilizing 5-amino-3-cyano-1-(2,6-dichloro-4-trifluoromethylphenyl)-4-trifluoromethylsulfinylpyrazole and thiodicarb.

3 Claims, 1 Drawing Sheet

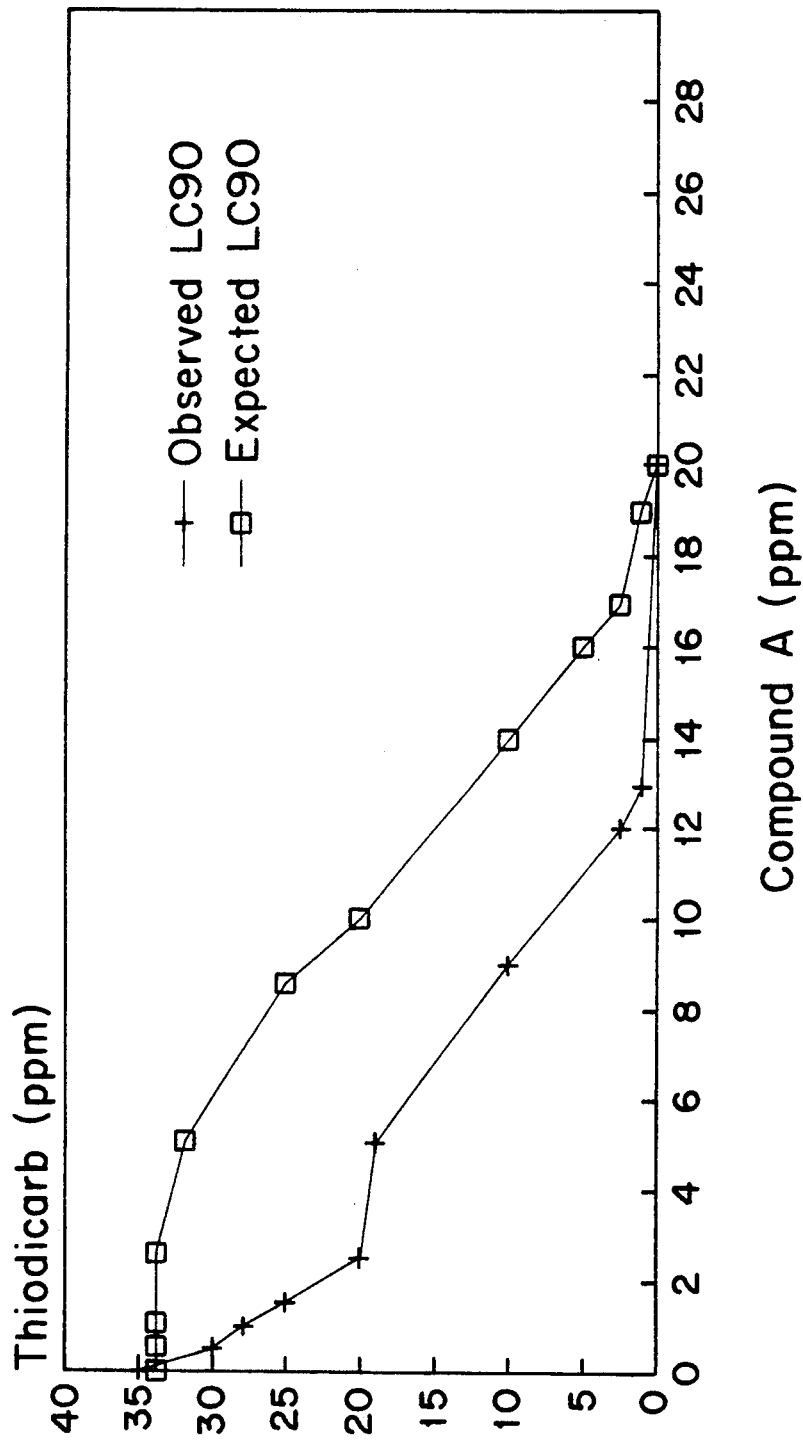

ARTHROPODICIDAL COMPOSITION COMPRISING THIODICARB AND A PHENYLPYRAZOLE

BACKGROUND OF THE INVENTION

1. Field of the Invention

The present invention relates to compositions containing mixtures of two or more pesticides and their use in the control of arthropod pests, particularly insects, in agriculture, forestry, animal health, public health and for the protection of stored products and structural timber.

2. Description of the Prior Art

5-Amino-3-cyano-1-(2,6-dichloro-4-trifluoromethylphenyl)-4-trifluoromethylsulfinylpyrazole (hereinafter referred to for convenience as "Compound A") and thiodicarb are both useful pesticides.

The preparation and use of, Compound A are described, for example, in European Patent Publication No. 0 295 117, published Dec. 14, 1988.

Thiodicarb is a well-known commercial product whose chemical name is N,N'-thiobis[(methylimino)-carbonyloxy]-bisethanimidothioic acid dimethyl ester.

Mixtures of different insecticides are commonly used to control mixed infestations of different insects, the constituent insecticides having different levels of effectiveness on different insect species. Thus, the chemicals need to be complementary in their beneficial action.

SUMMARY OF THE INVENTION

As a result of research and experimentation, it has been discovered, surprisingly, that Compound A can interact synergistically with thiodicarb when mixed with it to give a valuable improvement in the control of pests compared with that given by each insecticide alone.

The present invention relates to an arthropodicidal composition which comprises an arthropodicidally effective amount of (A) 5-amino-3-cyano-1-(2,6-dichloro-4-trifluoromethylphenyl)-4-trifluoromethylsulfinylpyrazole and (B) thiodicarb, which is N,N'-thiobis[(methylimino)-carbonyloxy]bisethanimidothioic acid dimethyl ester, in association with a pesticidally acceptable diluent or carrier. Preferably the weight ratio (A):(B) is between about 1:30 and about 13:1, and most advantageously between about 1:10 and about 2:1.

The invention also relates to a composition comprising an arthropodicidally effective amount of (A) 5-amino-3-cyano-1-(2,6-dichloro-4-trifluoromethylphenyl)-4-trifluoromethylsulfinylpyrazole and (B) thiodicarb, as a combined preparation for simultaneous, separate or sequential use in controlling arthropod pests at a locus.

The invention further relates to a method of controlling arthropod pests at a locus which comprises applying thereto an arthropodicidally effective amount of (A) 5-amino-3-cyano-1-(2,6-dichloro-4-trifluoromethylphenyl)-4-trifluoromethylsulfinylpyrazole and (B) thiodicarb.

The present invention thus provides for control of an improved range of insect species and also for enhanced control of insects susceptible to both compounds. This will permit an effective level of control to be maintained with a reduced amount of either or both constituents.

BRIEF DESCRIPTION OF DRAWING

The sole FIGURE of drawing is a *Spodoptera littoralis* isobologram depicting observed (+) and expected (□) LC90's for thiodicarb and Compound A in parts per million.

DETAILED DESCRIPTION OF THE PREFERRED EMBODIMENTS OF THE INVENTION

The valuable interaction of Compound A and thiodicarb has been established by known laboratory techniques as described in the following account, in which the effect is illustrated by the mixture of Compound A with thiodicarb, and its testing against a serious crop pest, the cotton leaf-worm *Spodoptera littoralis*.

Stock solutions were formulated using technical grade thiodicarb and Compound A in 50% v/v aqueous acetone to give concentrations of 500 ppm and 50 ppm (thiodicarb) and 50 ppm (Compound A). These solutions were further diluted with 50% aqueous acetone to yield a range of concentrations of Compound A alone of 10, 5, 2.5, 1 and 0.5 ppm and a range of concentrations of thiodicarb alone of 100, 50, 25, 10, 5, 2.5 and 1 ppm. The stock solutions were further subsampled and these subsamples so mixed, one of Compound A with one of thiodicarb, to give thirty-five different solutions consisting of each of the above-mentioned five concentrations of Compound A combined with each of the seven concentrations of thiodicarb. The above-mentioned forty-seven dilutions of the compounds, alone and in combination, were used as follows.

Cotton leaf discs were set in agar in petri dishes. Four replicate dishes were assigned to each treatment and were sprayed under a Potter tower with the appropriate test dilution. When dry, each dish was infected with ten 2nd instar larvae, and left to stand in a constant temperature (25° C.) room. After 3 days, the mean percentage mortalities of larvae were determined. These data were corrected using Abbot's correction against the mortalities in dishes treated with 50% aqueous acetone alone, which served as controls.

The results obtained were analyzed by the method of Tammes (1964, *Neth. J. Plant. Path.* 70, 73–80).

Dose response lines were prepared for Compound A in admixture with each of the thiodicarb concentrations, and for thiodicarb in admixture with each of the Compound A concentrations. From these lines were read $LC_{90}$ values for twelve combinations of the two compounds. Together with the $LC_{90}$ values for each compound alone, these provided the "observed" values plotted in the Figure.

The mortalities expected from given proportional mixtures were derived from the dosage mortality graphs for each compound separately, by the usual method for insecticides exhibiting joint independent action (Tammes, op. cit.). These provided the "expected" values plotted in the Figure.

The clear separation of the observed and expected lines in the Figure demonstrates an unexpected advantage of the mixtures in reducing the amounts of either compound required to achieve 90% mortality, thus indicating synergism or potentiation between the two constituents.

Other arthropods susceptible to control by use of Compound A and thiodicarb in accord with the present invention are disclosed in the aforementioned European Patent Publication No. 0 295 117, published Dec. 14, 1988.

The preferred proportions by weight of the two active constituents of the instant mixture range from about one part of Compound A with about 30 parts of thiodicarb to about 13 parts of Compound A with about 1 part of thiodicarb. A particular preference is for a mixture of Compound A and thiodicarb in proportions of from about 1 to 10 to about 2 to 1.

It should be understood that mixtures of other proportions are not excluded because, when several different pests are to be controlled at one site and time, greater or lesser amounts of one or the other constituent of the mixture may be required to control one or more particular pests, in addition to the benefit conferred by the synergistic activity of the mixture on other species present.

The compositions of the present invention are useful in the control of arthropod pests in agriculture, forestry, animal health, public health and for the protection of stored products and structural timber. Such applications are discussed in detail in the aforenoted European Patent Publication No. 0 295 117, published Dec. 14, 1988. Appropriate carriers or diluents for use in the compositions of the invention are likewise those detailed in said European Patent Publication No. 0 295 117, as would be apparent to one of ordinary skill in the art of pesticidal formulations.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, or obvious equivalents thereof.

What is claimed is:

1. An arthropodicidal composition comprising arthropodicidally effective amounts of (A) 5-amino-3-cyano-1-(2,6-dichloro-4-trifluoromethylphenyl)-4-trifluoromethylsulfinylpyrazole and (B) thiodicarb in a ratio of from about 1:30 to about 13:1, in association with a pesticidally acceptable diluent or carrier.

2. An arthropodicidal composition according to claim 1, comprising (A) and (B) in a ratio by weight of from about 1:10 to about 2:1.

3. A method of controlling arthropod pests at a locus, said method comprising applying to said locus an arthropodicidally effective amount of a composition as claimed in claim 2.

* * * * *